United States Patent [19]
Zuerner

[11] Patent Number: 5,091,301
[45] Date of Patent: Feb. 25, 1992

[54] DIAGNOSTIC AND EPIDEMIOLOGICAL NUCLEIC ACID PROBE FOR BOVINE LEPTOSPIROSIS

[75] Inventor: Richard L. Zuerner, Ames, Iowa

[73] Assignee: The Unites States of America as represented by the Secretary of Agriculture, Washington, D.C.

[21] Appl. No.: 327,064

[22] Filed: Mar. 22, 1989

[51] Int. Cl.$^5$ .............................................. C12Q 1/68
[52] U.S. Cl. ........................... 435/6; 435/7.22; 435/243; 435/320.1; 435/172.3; 935/3; 935/55
[58] Field of Search ................ 435/6, 5, 7.22, 243, 435/320.1; 424/89; 935/78

[56] References Cited

PUBLICATIONS

W. J. Terpstra et al., "Detection of Leptospiral DNA by Nucleic Acid Hybridisation with $^{32}$P-and Biotin-Labelled Probes", J. Med. Microbiol. 22: 23–28 (1986) (I).

W. J. Terpstra et al., "Detection of Leptospira Interrogans in Clinical Specimens by In Situ Hybridization Using Biotin-Labelled DNA Probes", J. Gen. Microbiol. 133: 911–914 (1987) (II).

B. D. Millar et al., "Detection of Leptospires in Biological Fluids Using DNA Hybridisation", Vet. Microbiol. 15: 71–78 (1987).

Rance B. LeFebvre, "DNA Probe for Detection of the Leptospira interrogans Serovar Hardjo Genotype Hardjo-Bovis", J. Clin. Microbiol. 25(11): 2236–2238 (Nov. 1987).

G. J. J. M. Van Eys et al., "DNA Hybridization with Hardjobovis-Specific Recombinant Probes as a Method for Type Discrimination of Leptospira interrogans Serovar Hardjo", J. Gen. Microbiol. 134: 567–574 (1988).

R. Zuerner et al., "Nucleic Acid Probes for the Detection of Leptospira interrogans Serovar Hardjo Type Hardjo-Bovis", Abstracts of the Annual Meeting of the American Society for Microbiology, Abstr. #D-66 (1988) (I).

R. L. Zuerner et al., "Repetitive Sequence DNA Probes Reveal Genetic Variability Among Leptospira interrogans Serovar Hardjo Type Hardjo-Bovis Isolates", Conference of Research Workers in Animal disease, Chicago, Ill., Abstr. #93 (Nov. 14–15, 1988) (II).

R. L. Zuerner et al., "Genetic and Protein Differences Separate Leptospira interrogans Serovars wolffi and romanica", Conference of Research Workers in Animal Disease, Chicago, Ill., Abstr. #94 (Nov. 14–15, 1988) (III).

Richard L. Zuerner et al., "Repetitive Sequence Element Cloned from Leptospira interrogans Serovar Hardjo Type Hardjo-Bovis Provides a Sensitive Diagnostic Probe for Bovine Leptospirosis", J. Clin. Microbiol. 26(12): 2495–2500 (Dec. 1988) (IV).

Zuerner et al., J. of Bacter. 170(10) 4548–54 (1988).
Bolin et al., Am. J. of Vet. Res. 50(7) 1001–3 (1989).
Nielsen et al., J. Clin. Microbiol. 27(12): 2724–29 (1989).
Le Febvre et al., Am. J. Vet. Res. 47(4): 959–63 (1986).
Ellis et al., Res. in Vet. Sci. 44: 375–79 (1988).
Marshall et al., Vet. Res. 117(25.6): 669–70 (1985).
Le Febvre (1987) DNA probe for detection of L. interrogans Serovar Hardjo Genotype Hardjo-Bovis J. Clin. Microb. 25(11) 2236.
Van Eys et al., (1988), DNA Hybridization with Hardjobovis-Specific recombinant probes for Discrimination-L-interrogans J. Gen. Micr. 134:567.

Primary Examiner—Amelia Burgess Yarbrough
Assistant Examiner—Miguel Escallon
Attorney, Agent, or Firm—M. Howard Silverstein; John D. Fado; Curtis P. Ribando

[57] ABSTRACT

A distinctive repetitive genomic element of Leptospira interrogans serovar hardjo-type hardjo-bovis permits distinguishing this pathogen type from other commonly found leptospires in North American cattle using single-stranded RNA probes. Plasmids carrying DNA templates for useful probes have been deposited as NRRL Accession Nos. B-18462, B-18463, and B-18464. The probes are sufficiently sensitive to detect hardjo-bovis in as few as $1 \times 10^2$ cells/ml. The diagnostic capabilities of the probes render them useful not only as herd management tools, but also in epidemiology studies designed to determine the origin and migration of L. interrogans isolates.

16 Claims, 2 Drawing Sheets

DIAGNOSTIC AND EPIDEMIOLOGICAL NUCLEIC ACID PROBE FOR BOVINE LEPTOSPIROSIS

BACKGROUND OF THE INVENTION

1. Field of the Invention

Leptospirosis, caused by *Leptospira interrogans*, is a disease of animals and humans which has a worldwide distribution. *L. interrogans* is an immunologically diverse species and contains several distinct genetic groups. At least six serologically distinct types (serovars) have been identified in North America and about 190 serovars throughout the world. In North America, the most common cause of bovine leptospirosis is *L. interrogans* serovar hardjo-type hardjo-bovis. Hardjo-bovis and the reference strain for serovar hardjo, hardjoprajitno, are both associated in cattle with the causation of abortions, stillbirths, production of weak offspring, and infertility. In addition, cattle infected with serovar hardjo develop persistent renal infections and shed leptospires in their urine. Exposure to urine containing hardjo-bovis is considered to be the primary source of infections within herds.

The two hardjo types can be differentiated by restriction endonuclease analysis of genomic DNA. However, the existence of similar antigens shared by hardjo-bovis and hardjoprajitno prevents these two bacteria from being differentiated by classical serological techniques.

This invention relates to a sensitive diagnostic probe for distinguishing hardjo-bovis from other pathogenic leptospires, particularly those which commonly infect domestic animals in North America.

2. Description of the Prior Art

Diagnosis of leptospirosis usually depends upon demonstration of serum antibodies. The serologic method of choice is the microscopic agglutination test reported by Cole et al. [Appl. Microbiol. 25: 976–980 (1973)]. However, interpretation of microscopic agglutination test results is often subjective and is complicated by numerous factors, including previous vaccination or infection and antigenic heterogeneity among *L. interrogans*. Since cattle infected with hardjo-bovis may fail to produce detectable antibodies, an accurate diagnosis of infection with hardjo-bovis requires direct demonstration of *L. interrogans* in tissues, blood, or urine. This is achieved either by bacteriological culture or by immunological techniques. Isolation of serovar hardjo from clinical specimens is labor intensive and inconsistent and requires weeks or months before results are obtained. Similarly, antigens may be degraded or blocked in some clinical specimens and thus prevent immunological detection of bacteria.

Several investigators have utilized DNA-DNA hybridization methods for rapid and reliable detection of *L. interrogans* in biological samples (blood, urine, and tissue homogenates) [B. D. Millar et al., Vet. Microbiol. 15: 71–78 (1987); W. J. Terpstra et al. I, J. Gen. Microbiol. 133: 911–914 (1987); and W. J. Terpstra et al. II, J. Med. Microbiol. 22: 23–28 (1986)]. The probes for these hybridizations consist of genomic DNA labeled by nick translation with radiolabeled or biotinylated nucleotides. Although these probes are specific for L. interrogans, they demonstrate extensive cross-hybridization among pathogenic serovars (Terpstra et al. II, supra). LeFebvre [J. Clin. Microbiol. 25: 2236–2238 (1987)] and Van Eys et al. [J. Gen. Microbiol. 134: 567–574 (1988)] disclose cloned DNA probes which differentiate hardjo-bovis from hardjoprajitno in DNA blot hybridization studies. These probes have not been well characterized, nor used to detect hardjo-bovis in biological material. Whereas the probe described by Lefebvre recognizes a discrete fragment of the hardjo-bovis genome which apparently exists as a single copy, probes described by Van Eys et al. may exist as several copies in the hardjo-bovis genome. The restriction enzyme maps of the probes described by Van Eys et al. are distinct from the probes described herein and are likely to detect different sequences than the probes of the invention.

SUMMARY OF THE INVENTION

I have now discovered a repetitive sequence element from hardjo-bovis and have cloned this fragment to develop a sensitive diagnostic single-stranded RNA probe for the detection of hardjo-bovis shed in the urine of infected cattle. This probe not only distinguishes hardjo-bovine from other pathogenic leptospires known to infect domestic animal species in North America, but it is also useful for distinguishing *L. interrogans* isolates of wildlife species as well. The probe is designed to bind specifically to the repetitive sequences contained within the hardjo-bovine genome while not cross-hybridizing with the genomic sequences of many other commonly encountered pathogenic leptospires.

In accordance with this discovery, it is an object of the invention to provide a probe for diagnosis of bovine leptospirosis, and particularly a probe which is specific for *L. interrogans* serovar hardjo-type hardjo-bovis. The probe is envisioned for use primarily as a replacement for bacteriological culture or fluorescent antibody screening techniques for the diagnosis of bovine leptospirosis.

It is also an object of the invention to provide plasmids carrying template DNA for transcribing the novel probes.

It is also an object of the invention to provide a sensitive, reliable, and rapid assay for hardjo-bovis suitable for large-scale herd screening.

More specifically, it is an object of the invention to identify infected cattle shedding hardjo-bovis in their urine.

Another object of the invention is to provide a probe for use in conjunction with restriction fragment length polymorphism (RFLP) technology as an epidemiological tool for distinguishing among different hardjo-bovis isolates.

A further object of the invention is to provide a diagnostic basis for designing an effective control program for hardjo-bovis in cattle herds.

Other objects and advantages of this invention will become readily apparent from the ensuing description.

Glossary

Figure 1:
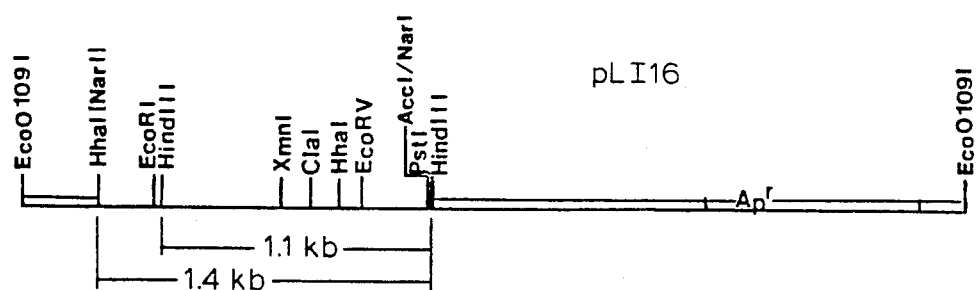
FIG. 1 is a schematic diagram depicting the restriction map of plasmid pLI16.

For purposes of this invention, the following standard abbreviations and terms used herein have been defined below. Also included are a listing of biological materials and reagents mentioned in the specification.

ABBREVIATIONS bp = basepairs
CAP = calf-alkaline phosphatase
DEAE = diethylaminoethanol
DNA = deoxyribonucleic acid
$dH_2O$ = distilled water
dpm = disintegrations per minute
EDTA = ethylenediaminetetraacetic acid
FA = fluorescent antibody
kb = kilobases (1000 basepairs)
kd = kilodalton
nt = nucleotide
PAGE = preparative agarose gel electrophoresis
REA = restriction enzyme analysis
RFLP = restriction fragment length polymorphism
RNA = ribonucleic acid
SDS = sodium dodecyl sulfate
SSC = 0.15M sodium chloride and 0.015M sodium citrate
ssRNA = single stranded RNA
TE = 10 mM Tris-HCl (pH 8.0), 1 mM EDTA

TERMS clone/cloning: in reference to DNA, the product or process of isolating a segment of DNA, linking it to a vector, and introducing it into a host for propagation.

cloning vector: a plasmid or other nucleic acid sequence which is able to replicate in a host cell characterized by one or a small number of restriction endonuclease recognition sites at which the sequence may be cut in a predetermined fashion, and which contains a marker suitable for use in the identification of transformed cells, e.g., tetracycline resistance or ampicillin resistance.

downstream: refers to the direction toward the 3' end of the DNA template.

DNA sequence: a linear series of nucleotides connected one to the other by phosphodiester bonds between the 3' and 5' carbons of adjacent pentoses.

transcription vector: a plasmid or other nucleic acid sequence comprising a polymerase promoter which is able to induce transcription of an inserted gene or sequence of heterologous DNA to single-stranded RNA.

gene: a segment of DNA which encodes a specific protein or polypeptide.

genome/genomic: referring to the complete set of genetic instructions for an organism as defined by the chromosomal nucleic acid.

heterologous DNA: a DNA sequence inserted within or connected to another DNA sequence which codes for polypeptides not coded for in nature by the DNA sequence to which it is joined.

hybridization: the pairing together or annealing of complementary single-stranded regions of nucleic acids to form double-stranded molecules.

infection: the introduction of bacteria or virus into cells or into a living organism wherein the bacteria or virus can replicate.

linker: synthetic oligonucleotide containing a site for a restriction enzyme.

multiple cloning site: a DNA sequence containing a multitude of different restriction enzyme sites.

nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U"). "N" is commonly used to represent any of these five bases.

phage: a bacteriophage; a virus which infects bacteria.

plasmid: a non-chromosomal, double-stranded DNA sequence capable of autonomous replication within a host cell.

polylinker: synthetic oligonucleotide containing multiple restriction enzyme sites.

probe: a nucleic acid sequence (DNA or RNA) that can be used to detect, by hybridization or complementary base-pairing, another nucleic acid sequence which is homologous or complementary.

promoter: a recognition sequence defining a site for binding of RNA polymerase and initiating transcription.

recombinant DNA molecule: a hybrid DNA sequence comprising at least two DNA sequences, the first sequence not normally being found together in nature with the second.

restriction site: A nucleotide sequence, usually 4 to 6 basepairs long, which is recognizes and susceptible to cleavage in a specific fashion by a restriction enzyme.

sequence: two or more DNA or RNA nucleotides in a given order.

serogroup: serological classification of Leptospira in which all strains in the same serogroup share a common "serogroup" antigen which is not present in strains outside of this serogroup.

serovar: serological classification of Leptospira in which strains within the same serogroup are serologically distinct from each other.

subclone: in reference to DNA, the product or process of cloning a portion of an already cloned DNA segment.

transcription: the process of producing messenger RNA (mRNA) from a structural gene.

transform: to change in a heritable manner the characteristics of a host cell in response to DNA foreign to that cell.

transformant/transformation system: a host cell such as E. coli which has been transformed by intoduction of a vector containing DNA foreign to the cell.

type: classification term for Leptospira in which two strains serologically classified as belonging to the same serovar may be differentiated on the basis of restriction endonuclease analysis.

vector: a derivative of a virus or plasmid constructed by recombinant DNA techniques and having a cloning site or sites for inserting new DNA sequences.

BIOLOGICAL MATERIALS AND REAGENTS

| | Source |
|---|---|
| Enzymes: | |

-continued

| | Source |
|---|---|
| T4 DNA ligase | New England BioLabs, Inc. |
| Genes: | |
| $Ap^r$ = ampicillin resistance gene | on pBSM13- |
| lacZ = β-galactosidase gene | on pBSM13- |
| Plasmids: Accession No. | |
| pBSM13- | Stratagene Corp. |
| pLI16 NRRL B-18461 | |
| pLI17 NRRL B-18462 | |
| pLI18 NRRL B-18463 | |
| pLI19 | |
| pLI20 NRRL B-18464 | |
| pUC19 | Bethesda Research Lab. Inc. |
| Polymerases: | |
| T3: bacteriophage T3 | Bethesda Research Lab. Inc. |
| T4: bacteriophage T4 | Bethesda Research Lab. Inc. |
| T7: bacteriophage T7 | New England BioLabs, Inc. |

| Restriction Enzymes: | Cleavage Site |
|---|---|
| AccI | AT |
| | 5'..GT CGAC..3' |
| ClaI | 5'..AT OGAT..3' |
| DraII | A C |
| | 5'..GG GNCCT..3' |
| EcoRI | 5'..G AATTC..3' |
| EcoRV | 5'..GAT ATC..3' |
| HhaI | 5'..GOG C..3' |
| HindIII | 5'..A AGCTT..3' |
| HinPI | 5'..G OGC..3' |
| NarI | 5'..GG CGCC..3' |
| PstI | 5'..CTGCA G..3' |
| SacI | 5'..GAGCT C..3' |
| XmnI | 5'..GAANN NNTTC..3' |
| Transformation Systems: | Source |
| *E. coli* strain JM107 | J. Neill, NADC |

The *L. interrogans* bacterial strains disclosed herein are summarized below in Table I.

TABLE I

| Bacterial Strains | | | |
|---|---|---|---|
| Organism and serogroup | Serovar | Type and/or strain | Source[a] |
| *L. interrogans* | | | |
| Sejroe | hardjo | Hardjo-bovis 93U | NADC |
| | hardjo | Hardjoprajitno | CDC/NADC |
| Canicola | portland-vere | Lt63-69 | CDC/NADC |
| Grippotyphosa | grippotyphosa | RM-52 | NADC |
| Icterohaemorrhagiae | copenhageni | M20 | CDC/NADC |
| Pomona | pomona | Kennewicki RM211 | NADC |
| Shermani | babudieri | CI40 | CDC |
| Icterohaemorrhagiae | birkini | Birkin | CDC |
| Canicola | broomi | patane | CDC |
| Pyrogenes | camlo | LT64-47 | CDC |
| Gryppotyphosa | canalzonae | cz188 | CDC |
| Ballum | castellonis | castelloni 3 | CDC |
| Celledoni | celledoni | celledoni | CDC |
| Cynopteri | cynopteri | 3522C | CDC |
| Javanica | flumininse | Aa3 | CDC |
| Autumnalis | fortbragg | fort bragg | CDC |
| Djasiman | gurungi | gurung | CDC |
| Louisiana | lanka | R740 | CDC |
| Australis | meunchen | Munchen c-90 | CDC |
| Bataviae | paidjan | paidjan | CDC |
| Sarmin | rio | Rr5 | CDC |
| Sejroe | romanica | LM294 | CDC |
| Pomona | tropica | Ca299U | CDC |
| Sejroe | wolffi | 3705 | CDC |
| *L. biflexa* | | | |
| Semaranga | Patoc | Patoc I | N. Charon |

[a]NADC strains are from the National Leptospirosis Reference Laboratory, National Animal Disease Center, Ames, IA. N. Charon is from West Virginia University, Morgantown. CDC strains are from K. Sulzer at the Center for Disease control, Atlanta, GA. CDC/NADC strains are originally from the Center for Disease Control.

DETAILED DESCRIPTION OF THE INVENTION

The original single-stranded RNA (ssRNA) probes of the invention were isolated as a result of discovering a repetitive sequence element which occurs collectively about 40–50 times within the hardjo-bovis genome and putative plasmid DNA. The 35–40 copies in the genome constitute about 2% of the genomic DNA. This element was identified by restriction endonuclease analysis (REA) of purified genomic DNA revealing a 1.4-kb NarI fragment which is present at a high copy number within the hardjo-bovis genome. This fragment was isolated by preparative agarose gel electrophoresis (PAGE) and thereafter cloned into the plasmid vector pUC19 to yield plasmid pLI16. Upon digestion of pLI16 with the restriction endonuclease HindIII, a 1,100 basepair (bp) fragment was recovered, and this fragment was subcloned into the RNA transcription vector, pBSM13-. Hybridization probes were synthesized from SacI-digested template DNA in the resulting plasmid, pLI17, by runoff transcription using phage T3 RNA polymerase and [$\alpha-^{32}P$]uridine triphosphate.

Contemplated within the scope of this invention are ssRNA probes which are complementary to, and will hybridize with, the repetitive element described above; that is, with the element comprising the 1.4-kb NarI fragment. Generally, the complementary portion of these probes should be at least about 250 bp in length so that the hybridization products can be visualized by autoradiograph or other assay. Probes having a length of about 250–350 are preferred for the reason that they tend to be more specific than longer probes in hybridizing to target DNA. For the purpose of differentiating hardjo-bovis from hardjoprajitno genomic DNA, at least about 80% homology is required between the probe and the target DNA. Noncomplementary sequences may flank the complementary portion of the probe provided that such sequences do not interfere with the hybridization of the DNA in the repetitive element to the extent that the hybridization products are not identifiable. Such extraneous sequences may arise at the 5' end of the probe as a result of transcription initiation by RNA polymerase within vector sequences prior to the heterologous DNA located 3' to the initiation site. It is likely that the terminal ends of the repetitive element are clipped by the NarI enzyme. Other endonucleases which would preserve these ends or a portion thereof could be substituted for the NarI in providing suitable template DNA for synthesis of the ssRNA probes.

For visualization by autoradiography, the probes are of course suitably labeled as with [$\alpha$—$^{32}$P]uridine triphosphate. This is readily achieved by labeling about 50% of the uridine triphosphate provided in the transcription medium during synthesis of the RNA probe.

Figure 3:
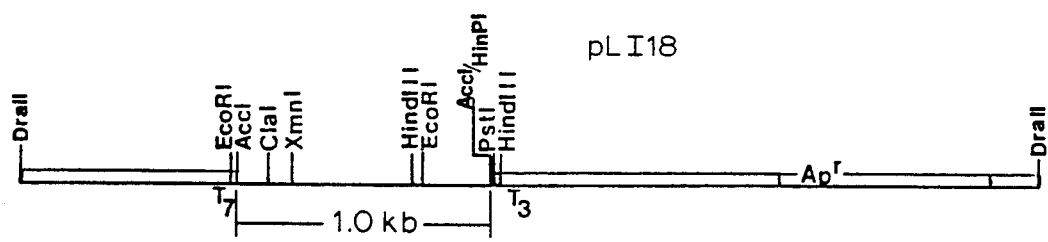
FIG. 3 is a schematic diagram depicting the restriction map of plasmid pLI18.
Figure 4:
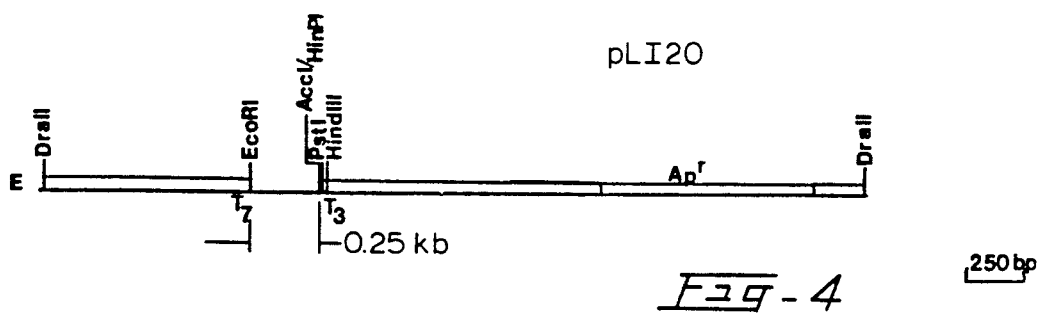
FIG. 4 is a schematic diagram depicting the restriction map of plasmid pLI20.
Figure 5:
FIG. 5 is an autoradiograph comparing genomic DNA fragments from *L. interrogans* serovars *wolffi* and *romanica* produced by digestion with EcoRI (lanes 1 and 2), HindIII (lanes 3 and 4), or XmnI (lanes 5 and 6) and which hybridize radiolabeled probe RNA.

Also contemplated by this invention are the templates and other progenitor DNA sequences for these probes, including plasmids useful in cloning and transcribing these sequences. An exemplary cloning plasmid is the above-mentioned pLI16 (FIG. 1) derived by insertion of the 1.4-kb NarI fragment into the pUC19 cloning vector which has been digested with NarI and AccI. This plasmid can be used to transform *E. coli* for expansion of the DNA insert. The above-described plasmid pLI17 (FIG. 2) illustrates a suitable plasmid for the synthesis of the ssRNA probes. As mentioned, it is constructed by excising the 1,100 bp HindIII fragment from the NarI insert of pLI16 and inserting this fragment into the transcription vector pBSM13-. In addition to the probe template, pLI17 comprises the promoter and other regulatory sequences for T3 and T7 RNA polymerases. Other transcription plasmids similarly derived from pLI16 include pLI18 (FIG. 3), pLI19 described in Example 5 and pLI20 (FIG. 4) described in Example 9 below. Plasmids pLI16, pLI18, and pLI20 have been deposited under the Budapest Treaty with the Agricultural Research Service Culture Collection in Peoria, IL, and have been assigned Accession Nos. NRRL B-18461, NRRL B-18462, NRRL B-18463 and NRRL B-18464, respectively.

It is envisioned that plasmids substantially equivalent to those which have been deposited could be readily derived by the skilled artisan by following the procedures described herein. Functional derivatives of these plasmids may also be prepared by making minor deletions, substitutions, or insertions in the nucleotides of the probe template DNA and/or by making deletions, substitutions, or insertions in the vector sequences.

The ssRNA probes are useful in DNA blot experiments utilizing restriction endonuclease digested DNA (Southern blots). Briefly, the *L. interrogans* DNA is immobilized on a membrane, and the membrane is washed in a solution of a radiolabeled probe. The probe binds to the appropriate segment of the repetitive element by complementary basepairing and can be detected by autoradiography. The probes can also be used in slot blot analysis of urine or other body fluid from infected livestock. Insofar as *L. interrogans* is also known to infect humans, it is understood that reference herein to body fluids and tissues of animals is meant to include the same from humans as well.

The strategy of repetitive sequence DNA used in this invention is attractive for the development of diagnostic probes, since the target sequences for probes are amplified naturally within the genome. This attribute enables detection of fewer organisms with the probes directed to repetitive sequence elements compared with probes directed to single-copy sequences. It is imperative for diagnostic purposes that the minimal number of cells detectable by a probe be relevant to the levels of bacteria shed by infected animals. As illustrated in Example 2 below, the probes contemplated herein detect as few as $1 \times 10^2$ cells/ml. These probes therefore detect typical levels of hardjo-bovis shed in the urine of cattle and offer an effective method to rapidly identify potential sources of hardjo-bovis infections within herds. The sensitivity and consistency of the repetitive element-based probe compares favorably with existing techniques but does not require prior cultivation of the organism.

The other significant attribute of diagnostic probes manifested by those of the invention is selectivity. As illustrated in Example 4, the subject probes demonstrates little detectable hybridization with any of the serovars commonly isolated from domestic animals in North America (serovars grippotyphosa, hardjo, copenhageni, pomona, and portland-vere) except for hardjo-bovis. Likewise, little cross-hybridization is observed with hardjoprajitno, the reference strain for serovar hardjo.

On the other hand, the ssRNA probes cross-hybridize with the DNA from several L. interrogans serovars isolated from wildlife. The presence of these serovars probably represent commensal infections. The selectivity against isolates of domestic animals and cross-reactivity with wildlife isolates render the ssRNA probes suitable for epidemiological studies in determining the origin and migration of a given isolate. Furthermore, the ability to type L. interrogans isolates, particularly those obtained from wildlife, using repetitive element-based probes, provides a more rapid typing system than using serological methods.

For distinguishing differences among isolates in epidemiology studies of hardjo-bovis infections, the enzymes EcoRI, HhaI, and XmnI were found to be most suitable for digesting the genomic DNA prior to probing. For RFLP analysis for identifying serovars, the enzymes EcoRI, ClaI, BamHI, HindIII, and XmnI were found to be most useful.

The following examples are intended only to further illustrate the invention and are not intended to limit the scope of the invention which is defined by the claims.

EXAMPLE 1

Isolation of the Repetitive Element

The repetitive element was cloned by digesting 10 μg *L. interrogans* serovar hardjo-type hardjo-bovis strain 93U DNA (prepared by the method of Thiermann et al., [J. Clin. Microbiol. 21: 585–587 (1985)] with approximately 10 units of restriction endonuclease NarI at 37° C. for 6 hr in a solution containing 10 mM Tris-Hcl (pH 7.4), 10 mM MgCl$_2$, 10 mM 2-mercaptoethanol. The resulting restriction fragments were resolved in a 1% agarose gel buffered with 89 mM Tris, 89 mM boric acid, 2 mM EDTA at 50 V for 20 hr. The gel was stained with 1 μg ethidium bromide/ml for 1 hr and the DNA visualized by illumination with ultraviolet light. The 1.4 kb NarI fragment was excised from the gel and transferred to an NA-45 DEAE membrane (Schleicher and Schuell, Inc.) by electrophoresis at 100 V for 2 hr. The membrane was rinsed with electrophoresis buffer and the DNA eluted in 200 μl, 1.0M NaCl, 0.1 mM EDTA, 20 mM Tris-Hcl (pH 8.0), at 60° C. for 2 hr. The membrane was discarded and the solution volume brought to 500 μl with distilled water (dH$_2$O). This DNA was precipitated with 50 μl 3M sodium acetate (pH 5.2), and 1 ml 95% ethanol, and harvested by centrifugation at 11,000×g for 15 min. The precipitate was suspended in 500 μl TE [10 mM Tris-HCl (pH 8.0), 1 mM EDTA] and extracted twice with 500 μl phenol-chloroform-isoamyl alcohol (50:50:1). DNA was recovered from the aqueous phase by precipitation with sodium acetate and ethanol, and the precipitate washed with 500 μl 70% ethanol. The precipitate was suspended in 20 μl dH$_2$O and 10 μl (ca. 100 ng) was mixed with approximately 100 ng pUC19 which had previously been digested with NarI and AccI, and treated with calf-alkaline phosphatase (CAP). This mixture was treated with 400 units of phage T4 DNA ligase in a 20 μl reaction volume containing 50 mM Tris-Hcl (pH 7.8), 10 mM MgCl$_2$, 20 mM dithiothreitol, 1 mM adenosine triphosphate, and 50 μg bovine serum albumin/ml at 16° C. for 6 hr. The mixture was heated at 65° C. for 15 min then used to transform *Escherichia coli* JM107 to ampicillin resistance by standard technique. Transformants harboring recombinant plasmids were identified by inactivation of the vector-encoded lacZ gene by using the chromogenic lactose analog 5-bromo-4-chloro-3-indolyl-β-D-galactopyranoside [J. Messing, Methods Enzymol. 101: 20–78 (1983)]. Plasmid DNA was prepared from randomly picked transformants using an alkaline lysis technique [D. Ish-Horowitcz et al., Nucl. Acids Res. 9: 2989–2996 (1981)] and examined by REA. One of these clones, pLI16 was used for subsequent analysis and subcloning. A schematic restriction enzyme map of pLI16 is shown in FIG. 1, wherein the ampicillin resistance gene is indicated as "Ap$^r$." Vector DNA sequences are shown as double lines, whereas cloned hardjo-bovis DNA is shown as single lines.

Figure 2:
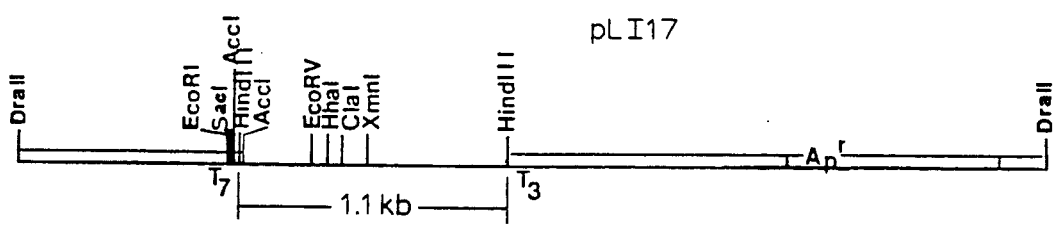
FIG. 2 is a schematic diagram depicting the restriction map of plasmid pLI17.

Construction of Probe DNA Template by Subcloning Hardjo-Bovis DNA into pBSM13-.

pLI16 (ca. 10 μg) as prepared above was digested with 10 units of HindIII in 100 μl of a solution containing 50 mM NaCl, 50 mM Tris-HCl (pH 8.0), 10 mM MgCl$_2$ at 37° C. for 6 hr. The digestion products were fractionated by electrophoresis in a 1% agarose gel and the 1100 bp HindIII fragment isolated onto NA-45 membrane as described above. The DNA was eluted from the NA-45 membrane, concentrated, and ligated to HindIII-digested, CAP-treated RNA transcription vector pBSM13- by the method described above for ligating the bacterial DNA to the digested pUC19. Plasmid pBSM13- contains the RNA polymerase promoters for both bacteriophage T3 and T7. *E. coli* JM107 was transformed to ampicillin resistance with the ligation mixture and plasmid DNA isolated from randomly picked transformants and examined by REA. One plasmid, pLI17, was used for subsequent probe synthesis. The restriction map of pLI17 is shown in FIG. 2, wherein T7 and T3 represent the T7 and T3 promoters, respectively.

Preparation of ssRNA Probe

Five micrograms of purified pLI17 DNA was digested with 5 units of restriction endonuclease SacI at 37° C. for 2 hr in a solution containing 10 mM Tris-HCl (pH 7.4), 10 mM MgCl$_2$, 10 mM 2-mercaptoethanol, and a final volume of 50 μl. The plasmid DNA was precipitated by addition of 5 μl 3 M sodium acetate (pH 5.2) and 200 μl 95% ethanol, harvested by centrifugation for 15 min at 11,000×g, and then washed with 500 μl 70% ethanol. The precipitated DNA was dissolved in solution by sequential addition of 2 μl 0.1M dithiothreitol, 2.4 μl 0.1 mM uridine triphosphate, 4 μl/2.5 mM each ATP, GTP, CTP, 1 μl dH$_2$O, 5 μl [α−$^{32}$P]uridine triphosphate [ca. 650 Curies (Ci)/mmol, 10 mCi/ml)], 4 μl buffer [200 mM Tris-HCl (pH 8.0), 40 mM MgCl$_2$, 10 mM spermidine, 125 mM NaCl] and the reactions initiated with 10 units of phage T3 RNA polymerase. After incubating the reaction at 37° C. for 1 hr, it was terminated by addition of 1 μl 20% sodium lauryl sulfate, 75 μl dH$_2$O, 10 μl 3M sodium acetate (pH 5.2), and 500 μl 95% ethanol. The DNA template was harvested by centrifugation and washed as before. The resultant 1,100 bp radiolabeled single-stranded RNA (ssRNA) probe was suspended in 100 μl TE, heated at 85° C. for 5 min, and then quickly chilled on ice in preparation for use in the hybridization analyses described below in Example 2.

EXAMPLE 2

Diagnostic Screening

Positive urine samples were collected from four experimentally infected animals demonstrating no clinical signs of disease 4, 8, and 12 wk after exposure to hardjo-bovis and from one naturally infected cow. In this experiment, the negative-control sample was a composite from nine animals collected prior to experimental infection.

The slot blot analyses were performed by using a modification of the procedure described by Millar et al. [Vet. Microbiol. 15: 71–78 (1987)]. Bacteria were concentrated from 1–10 ml of the collected urine by centrifugation at 11,000×g for 5–15 min. The cells were suspended in 100 μl phosphate buffered saline, mixed with an equal volume of 0.5M NaOH, 1.5M NaCl, and incubated at room temperature for 1 hr. Solutions were neutralized with 200 μl 1M Tris-HCl (pH 8.0), 1.5M NaCl and filtered through nylon membrane filters (Hybond-N, Amersham Corporation) using a commercially available filtering apparatus (Minifold II, Schleicher and Schuell Corporation). The filters were rinsed with 2×SSC (1×SSC: 0.15M NaCl, 0.015M sodium citrate), and air dried. Membranes were incubated for a minimum of 2 hr at 61° C. in hybridization solution [6×SSC, 5×Denhardts solution (1×Denhardts: 0.02% Ficoll, 0.02% polyvinylpyrrolidone, 0.02% bovine serum albumin), 1% sodium lauryl sulfate, 100 μg denatured salmon sperm DNA/ml, and 100 μg yeast RNA/ml]. This prehybridization solution was discarded, replaced by fresh hybridization solution containing the radiolabeled ssRNA probe prepared in Example 1 and incubated overnight at 61° C. These filters were then washed twice in 2×SSC at room temperature for 15 min each, twice in 2×SSC at 61° C. for 15 min each, and twice in 2×SSC, 0.1% SDS at 61° C. for 30 min each. Blots were used to expose autoradiographic film (Eastman Kodak, Inc.) at −80° C. for 1–3 da before developing.

Autoradiographic images were quantitated by scanning the autoradiographs with a laser densitometer (Ultrascan XL, LKB Instruments, Inc., Rockville, MD) and subsequent analysis with Gelscan XL software (LKB Instruments).

To quantitate the amount of hardjo-bovis shed in the urine of infected cattle, autoradiographic signals obtained in the urine samples were compared to signals obtained with specific cell numbers. The cell concentration of cultured bacteria was determined with a Petroff-Hauser counting chamber by using dark-field microscopy. Cell concentrations were adjusted to $5 \times 10^7$ cells per ml with phosphate-buffered saline and serially diluted, by using twofold dilutions, to $2.5 \times 10^4$ cells per ml. Samples (100 µl) of these diluted cell suspensions were mixed with 100 µl of 0.5M NaOH-1.5M NaCl and incubated for 1 hr at room temperature. These suspensions were neutralized with 200 µl of 1M Tris hydrochloride-1.5M NaCl, pH 8.0, and 40 µl of the suspension was applied to Hybond-N by using a slot blot apparatus (Schleicher & Schuell).

The results of this experiment are summarized in Table II below and demonstrate that the pLI17-derived probe detects hardjo-bovis shed in urine from infected animals. The number of leptospires detected in the urine of infected animals ranged from $<1 \times 10^2$ cells per ml to approximately $3 \times 10^4$ cells per ml. Most but not all of the urine samples tested were found to contain hardjo-bovis either by culture or by fluorescent antibody (FA). Additionally, culture and FA results of urine samples from cow 86 taken at other times during the infection were positive, thus confirming that this cow was infected and shedding L. interrogans in its urine.

TABLE II

Test of pLI17 Probe with Cattle Urine Samples

| Sample | Time postinfection (mo)[a] | Concn (cells/ml)[b] | Culture[c] | FA[d] |
|---|---|---|---|---|
| Negative control |  | $<1 \times 10^2$ | — | — |
| Cow 103 | 1 | $3 \times 10^2$ | + | + |
|  | 2 | $4 \times 10^3$ | — | + |
|  | 3 | $1 \times 10^2$ | + | + |
| Cow 79 | 2 | $7 \times 10^3$ | + | + |
|  | 3 | $2 \times 10^3$ | — | + |
| Cow 86 | 2 | $4 \times 10^2$ | — | — |
|  | 3 | $1 \times 10^2$ | — | — |
| Cow 80 | 2 | $3 \times 10^4$ | + | + |
| 40U |  | $4 \times 10^3$ | + | + |

[a]Time following experimental infection of cattle with hardjo-bovis. 40U was naturally infected, and time of exposure could not be determined.
[b]Bacterial cell concentrations in urine normalized to cells per milliliter as determined with pLI17.
[c]Results of attempts to culture urine samples.
[d]Results of fluorescent antibody with anti-hardjo-bovis conjugate.

EXAMPLE 3

Sensitivity and Selectivity Comparison of ssRNa Probe and DNA-Probe

The sensitivity of the radiolabeled ssRNA probe synthesized from pLI17 in Example 1 was compared with that of a radiolabeled genomic DNA probe. Various serovars and types of L. interrogans and L. biflexa were cultured and then were serially diluted from $5 \times 10^7$ cells per ml to $2.5 \times 10^4$ cells per ml and lysed. The DNA was denatured, and a portion of these suspensions was filtered through a nylon membrane. The immobilized DNA was used to hybridize either the pLI17-derived radiolabeled ssRNA probe or serovar hardjo-type hardjo-bovis genomic DNA radiolabeled by nick translation. Both of these probes were radiolabeled to specific activities of approximately $10^9$ dpm/µg of nucleic acid. The resulting autoradiographs demonstrated that the pLI17-generated probe can detect as few as $1 \times 10^3$ hardjo-bovis cells, while the detection limit for the radiolabeled genomic DNA probe was approximately $4 \times 10^3$ cells. The level of specificity of these two probes for hardjo-bovis was assessed by quantitating autoradiographic signals by scanning laser densitometry and then comparing the values obtained in heterologous reactions with those obtained in homologous reactions. The results of this analysis (Table III) indicate that the pLI17-derived probe is more specific for hardjo-bovis than the genomic hardjo-bovis DNA probe. Both probes were species specific, as where was no detectable cross-hybridization between either probe and the saprophyte. L. biflexa serovar patoc.

TABLE III

Quantitative Comparison of pLI17 and Genomic DNA Probe Specificities

| | % Hybridization with nucleic acid probe from: | |
|---|---|---|
| Organism and serovar[a] | pLI17[b] | Hardjo-bovis[c] |
| L. interrogans | | |
| Hardjo-type hardjo-bovis | 100 | 100 |
| Hardjo-type hardjoprajitno | 8 | 11 |
| Pomona-type kennewicki | 2 | 5 |
| Grippotyphosa | 5 | 16 |
| Portland-vere | 1 | 27 |
| Copenhageni | 1 | 11 |
| L. biflexa | | |
| Patoc | <1 | <1 |

[a]Samples containing $2.5 \times 10^5$ cells.
[b]Comparison of autoradiographic signals with signals obtained with hardjo-bovis using pLI17 probe.
[c]Comparison of autoradiographic signals with signals obtained with hardjo-bovis using hardjo-bovis genomic probe.

EXAMPLE 4

Selectivity of pLI17-Derived ssRNA Probe Against Domestic Animal Isolates

The selectivity of the ssRNA probes synthesized from pLI17 as described in Example 1 for the 1.4 kb NarI repetitive fragment characteristic of hardjo-bovis was demonstrated by Southern blot analysis. Genomic DNA (2.5 µg) isolated from each of L. interrogans serovars hardjo-type hardjo-bovis, hardjo-type hardjo-prajitno, pomona-type kennewicki, grippotyphosa, copenhageni, and portland-vere was digested with NarI. Digestion products were fractionated by electrophoresis at 50 V overnight in 0.7% agarose gels as described previously. The gels were treated with 0.5M NaOH, 1.5M NaCl for 1-2 hr, and then neutralized with 1M Tris-HCl (pH 8.0), 1.5M NaCl for 1-2 hr. DNA was blotted to nylon membranes by capillary action overnight with $20 \times SSC$. The nylon membranes were washed with $2 \times SSC$, air dried, prehybridized, and hybridized with the $^{32}P$-labeled ssRNA probe as described in Example 2. The membranes were washed as in Example 2 with an additional wash of $0.2 \times SSC$ at 61° C. The membranes were used to expose AR film at −80° C. for 1 hr before developing. The autoradiographs indicated at least 12 distinct bands for the hardjo-bovis DNA and no bands for any of the other serovar or type DNA assayed.

EXAMPLE 5

Preparation of pLI18- and pLI19-Derived Probes

Following the procedure of Example 1 for construction of a probe DNA template and preparation of ssRNA probe, pLI16 was digested with HinPI, and a recovered 1,000 bp fragment was inserted into the AccI site of pBSM13-. The two selected plasmids, pLI18 and pLI19 carry this fragment in opposite orientations. pLI18 is shown schematically in FIG. 3.

Probes generated by runoff transcription of Eco-RI-digested pLI18 detect some fragments which are not detectable with pLI17-derived probes since these fragments are homologous to the small EcoRI-NarI fragment of the repetitive element missing in pLI17.

EXAMPLE 6

Selectivity of the pLI18-Derived ssRNA Probe Against Wildlife Isolates

The ability of the ssRNA probe from pLI18 prepared in Example 1 to distinguish two *L. interrogans* wildlife isolates, serovars wolffi and romanica, from one another was determined. These serovars are genetically similar and cannot be differentiated by restriction endonuclease analysis of genomic DNA. Genomic DNA from cultured cells of these serovars was prepared by the method of Thiermann as referenced in Example 1 and digested with EcoRI, HindIII, or XmnI. The resulting fragments were fractionated by agarose gel electrophoresis, blotted to a nylon membrane, and probed with the radiolabeled probe as in Example 2, except the hybridization and washing were conducted at 58° C. The subtle differences between these two serovars could be detected as illustrated by the autoradiograph of FIG. 5. The odd-numbered lanes represent wolffi, and the even-numbered lanes represent romanica. The DNA of lanes 1 and 2 was digested with EcoRI, that of lanes 3 and 4 was digested with HindIII, and that of lanes 5 and 6 was digested with XmnI. The arrows depict bands representing fragments not characteristic of the related serovar.

EXAMPLE 7

Differentiation of Hardjo-Bovis Isolates with pLI17-Derived Probe

Genomic DNA (2.5 μg) from six hardjo-bovis isolates originally obtained from cattle in Iowa, Colorado, Florida, Alberta (Canada), Switzerland, and Chile were digested with HhaI or EcoRI. The digestion products were electrophoresed in agarose, blotted to a nylon membrane, and probed with the pLI17-derived probe, all as described in Example 4. Autoradiographs showed distinct patterns among the isolates for each of the enzyme digests. This experiment demonstrates the usefulness of the ssRNA probes in differentiating isolates from different geographical locations.

EXAMPLE 8

Differentiation of *L. interrogans* Serovars

Genomic DNA (2.5 μg) from *L. interrogans* serovars *meunchen, fortbragg,* castellonis, paidjan, lanka, broomi, celledoni, cynopteri, rio, gurungi, canalzonae, birkini, flumininse, tropica, camlo, babudieri were digested with EcoRI, electrophoresed in a 0.7% agarose gel, and blotted to a nylon membrane, essentially as described in Example 6. Radiolabeled probes were synthesized by the procedure of Example 1 except the pLI17 plasmid was digested with EcoRV and the transcription was initiated with phage T7 RNA polymerase. The autoradiograph hybridization pattern representing each of the 16 serovars was distinct, thereby providing a basis for distinguishing one from the other.

EXAMPLE 9

Preparation of pLI20 Derived Probe

Following the procedure of Example 1 for construction of a probe DNA template and preparation of ssRNA probe, pLI18 was digested with EcoRI and a recovered 3,450 bp fragment was self-ligated using T4 DNA ligase. The resulting plasmid, pLI20, differs from pLI18 by the deletion of a 750 bp EcoRI fragment. pLI20 contains approximately 250 bp of hardjo-bovis DNA inserted between the EcoRI and AccI sites of pBSM13- and is shown schematically in FIG. 4. Radiolabeled ssRNA probes are synthesized from HinPI-digested pLI20 by run-off transcription with T7 phage RNA polymerase.

It is understood that the foregoing detailed description is given merely by way of illustration and that modification and variations may be made therein without departing from the spirit and scope of the invention.

I claim:

1. A single stranded RNA probe which will hybridize with a 1.4-kb NarI fragment having a restriction enzyme pattern as shown in FIG. 1 and contained within a repetitive genomic element of *Leptospira interrogans* serovar hardjo-type hardjo-bovis, wherein said probe is the runoff transcription product of *Leptospira interrogans* template DNA obtained as an endonuclease digest of a plasmid selected from the group consisting of pLI16 (NRRL B-18461), pLI17 (NRRL B-18462), pLI18 (NRRL B-18463, and pLI20 (NRRL B-18464).

2. The RNA probe of claim 1 wherein said probe is about 250 to 350 basepairs in length.

3. The RNA probe of claim 1 wherein said probe is the runoff transcription product of the SacI-digested pLI17 plasmid corresponding to NRRL Accession No. B-18462.

4. The RNA probe of claim 1 wherein said probe is the runoff transcription product of the EcoRI-digested pLI18 plasmid corresponding to NRRL Accession No. B-18463.

5. The RNA probe of claim 1 wherein said probe is the runoff transcription product of the HinPI-digested pLI20 plasmid corresponding to NRRL Accession No. B-18464.

6. The RNA probe of claim 1 wherein said probe is radiolabeled.

7. A method of diagnosing infection by *Leptospira interrogans* serovar hardjo-type hardjo-bovis bacterium in a body fluid or tissue of an animal comprising:

a. recovering bacterial DNA from said fluid or tissue;

b. probing said DNA with a RNA probe which will hybridize with a 1.4-kb NarI fragment having a restriction enzyme pattern as shown in FIG. 1 and contained within a repetitive genomic element of said hardjo-bovis bacterium, wherein said probe is the runoff transcription product of *Leptospira interrogans* template DNA obtained as an endonuclease digest of a plasmid selected from the group consisting of pLI16 (NRRL B-18461), pLI17 (NRRL B-18462), pLI18 (NRRL B-18463, and pLI20 (NRRL B-18464); and c. analyzing for hybridized DNA.

8. The method of claim 7 wherein said probe is about 250 to 350 basepairs in length.

9. The method of claim 7 wherein said probe is the runoff transcription product of the SacI-digested pLI17 plasmid corresponding to NRRL Accession No. B-18462.

10. The method of claim 7 wherein said probe is the runoff transcription product of the EcoRI-digested pLI18 plasmid corresponding to NRRL Accession No. B-18463.

11. The method of claim 7 wherein said probe is the runoff transcription product of the HinPI-digested pLI20 plasmid corresponding to NRRL Accession No. B-18464.

12. The method of claim 7 wherein said probe is radiolabeled.

13. The method of claim 7 wherein said animal is a species of domestic cattle.

14. A DNA template for a probe which will hybridize with a 1.4-kb NarI fragment having a restriction enzyme pattern as shown in FIG. 1 and contained within a repetitive genomic element of *Leptospira interrogans* serovar hardjo-type hardjo-bovis, wherein said template is a plasmid selected from the group consisting of pLI16 (NRRL B-18461), pLI17 (NRRL B-18462), pLI18 (NRRL B-18463, and pLI20 (NRRL B-18464).

15. A DNA template as described in claim 14 wherein said template is plasmid pLI20.

16. A DNA template as described in claim 14 wherein said template is plasmid pLI17.

* * * * *